(12) United States Patent
Lee et al.

(10) Patent No.: US 6,849,072 B2
(45) Date of Patent: Feb. 1, 2005

(54) METHODS AND APPARATUS FOR THERMALLY AFFECTING TISSUE

(75) Inventors: Albert S. Lee, Boston, MA (US); Walter J. Koroshetz, Milton, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 09/824,625

(22) Filed: Apr. 2, 2001

(65) Prior Publication Data

US 2002/0077682 A1 Jun. 20, 2002

Related U.S. Application Data

(60) Provisional application No. 60/195,571, filed on Apr. 7, 2000.

(51) Int. Cl.[7] .............................................. A61B 18/18
(52) U.S. Cl. ........................ 606/21; 606/23; 607/113
(58) Field of Search ............................ 606/20–31, 41; 607/101–105, 107, 113, 96

(56) References Cited

U.S. PATENT DOCUMENTS

| | | | |
|---|---|---|---|
| 3,320,414 A | | 5/1967 | Bowland |
| 3,504,674 A | | 4/1970 | Swenson et al. |
| 3,736,936 A | | 6/1973 | Basiulis et al. |
| 3,776,241 A | | 12/1973 | Magilton et al. |
| 3,897,790 A | | 8/1975 | Magilton et al. |
| 4,010,795 A | * | 3/1977 | Stenberg ...................... 165/46 |
| 4,207,897 A | | 6/1980 | Lloyd et al. |
| 4,781,193 A | | 11/1988 | Pagden et al. |
| 5,108,407 A | * | 4/1992 | Geremia et al. ............... 604/57 |
| 5,207,674 A | | 5/1993 | Hamilton |
| 5,281,215 A | * | 1/1994 | Milder ........................ 606/20 |
| 5,304,214 A | | 4/1994 | DeFord et al. |
| 5,308,319 A | | 1/1995 | Saito et al. |
| 5,429,582 A | | 7/1995 | Williams |
| 5,456,702 A | * | 10/1995 | Falk ............................ 607/105 |
| 5,474,533 A | | 12/1995 | Ward et al. |
| 5,496,271 A | * | 3/1996 | Burton et al. ................. 607/27 |
| 5,531,776 A | | 7/1996 | Ward et al. |
| 5,540,711 A | | 7/1996 | Kieturakis et al. |
| 5,607,443 A | | 3/1997 | Kieturakis et al. |
| 5,609,620 A | * | 3/1997 | Daily ........................ 607/105 |
| 5,611,767 A | | 3/1997 | Williams |
| 5,624,392 A | | 4/1997 | Saab |
| 5,643,207 A | | 7/1997 | Rise |
| 5,716,386 A | | 2/1998 | Ward et al. |
| 5,730,756 A | | 3/1998 | Kieturakis et al. |
| 5,733,280 A | * | 3/1998 | Avitall ........................ 606/23 |
| 5,772,680 A | | 6/1998 | Kieturakis et al. |
| 5,817,123 A | | 10/1998 | Kieturakis et al. |
| 5,868,735 A | * | 2/1999 | Lafontaine ................... 606/21 |
| 5,871,498 A | | 2/1999 | Jervis et al. |

(List continued on next page.)

FOREIGN PATENT DOCUMENTS

WO      WO 99/34758       7/1999

OTHER PUBLICATIONS

Fay, T. "Early Experiences with Local and Generalized Refrigeration of the Human Brain," *J. Neurosurg.*, 16:239–60(1959).

(List continued on next page.)

*Primary Examiner*—Michael Peffley
(74) *Attorney, Agent, or Firm*—Nutter McClennen & Fish LLP

(57) ABSTRACT

Methods and apparatus are provided for thermally affecting tissue via either a closed or open device. In each of the closed device embodiments, thermally transmissive fluid is circulated and distributed through into a device, an outer surface of which is in direct thermal contact with a region of tissue to thermally affect the tissue. In each of the open device embodiments, thermally transmissive fluid is circulated through a device and systematically deployed directly onto a region of tissue to irrigate, and, therefore, thermally affect the tissue.

16 Claims, 6 Drawing Sheets

U.S. PATENT DOCUMENTS

| | | | |
|---|---|---|---|
| 5,891,134 A * | 4/1999 | Goble et al. .................. 606/27 |
| 5,916,212 A | 6/1999 | Baust et al. |
| 5,916,242 A | 6/1999 | Schwartz |
| 5,957,963 A | 9/1999 | Dobak, III |
| 5,972,924 A | 10/1999 | Keep et al. |
| 6,004,337 A | 12/1999 | Kieturakis et al. |
| 6,015,382 A | 1/2000 | Zwart et al. |
| 6,015,421 A | 1/2000 | Echeverry et al. |
| 6,022,308 A | 2/2000 | Williams |
| 6,045,532 A | 4/2000 | Eggers et al. |
| 6,051,019 A | 4/2000 | Dobak, III |
| 6,073,051 A | 6/2000 | Sharkey et al. |
| 6,083,148 A | 7/2000 | Williams |
| 6,096,068 A | 8/2000 | Dobak, III et al. |
| 6,106,518 A * | 8/2000 | Wittenberger et al. ........ 606/23 |
| 6,129,736 A | 10/2000 | Jervis et al. |
| 6,132,415 A | 10/2000 | Finch et al. |
| 6,168,608 B1 | 1/2001 | Echeverry et al. |
| 6,224,624 B1 | 5/2001 | Lasheras et al. |
| 6,238,428 B1 | 5/2001 | Werneth et al. |
| 6,248,126 B1 * | 6/2001 | Lesser et al. ................. 606/20 |
| 6,251,129 B1 | 6/2001 | Dobak, III et al. |
| 6,251,130 B1 | 6/2001 | Dobak, III et al. |
| 6,283,959 B1 * | 9/2001 | Lalonde et al. ............... 606/21 |
| 6,546,932 B1 * | 9/2001 | Lalonde et al. ............. 128/898 |
| 6,322,559 B1 * | 11/2001 | Daulton et al. ............... 606/41 |
| 6,383,210 B1 * | 5/2002 | Magers et al. ................ 606/20 |

OTHER PUBLICATIONS

Connolly, J.E., etal., "The Protective Effect of Hypothermia in Cerebral Ischemia: Experimental and Clinical Application by Selective Brain Cooling in the Human," *Surgery*, 1:15–24(1962).

Kindt, G.W. and Youmans, J.R., "Regional Hypothermia Produced by Cooling the Blood within the Intact Artery," *Surgical Forum*, 17:406–7(1966).

Locke, G.E., etal., "Profound Selective Arterial Cooling of Brain without Pump or Oxygenator," *Surgical Forum*, 16:421–22 (1965).

Negrin, J., "The Hypothermostat: An instrument to Obtain Local Hypothermia of the Brain or Spinal Cord," *International Surgery*, 54(2):93–106(1970, Aug.).

* cited by examiner

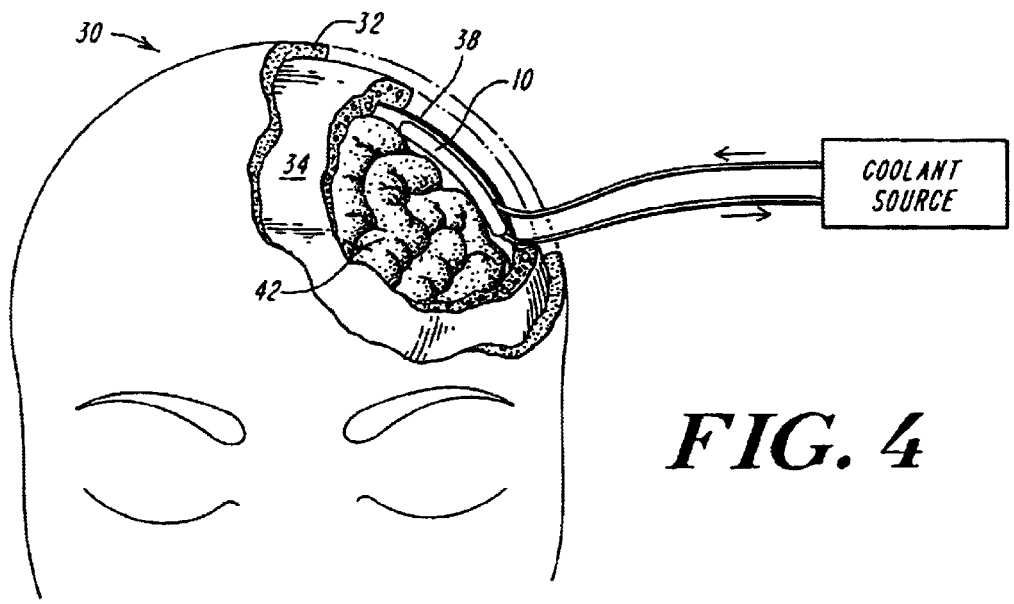
*FIG. 4*
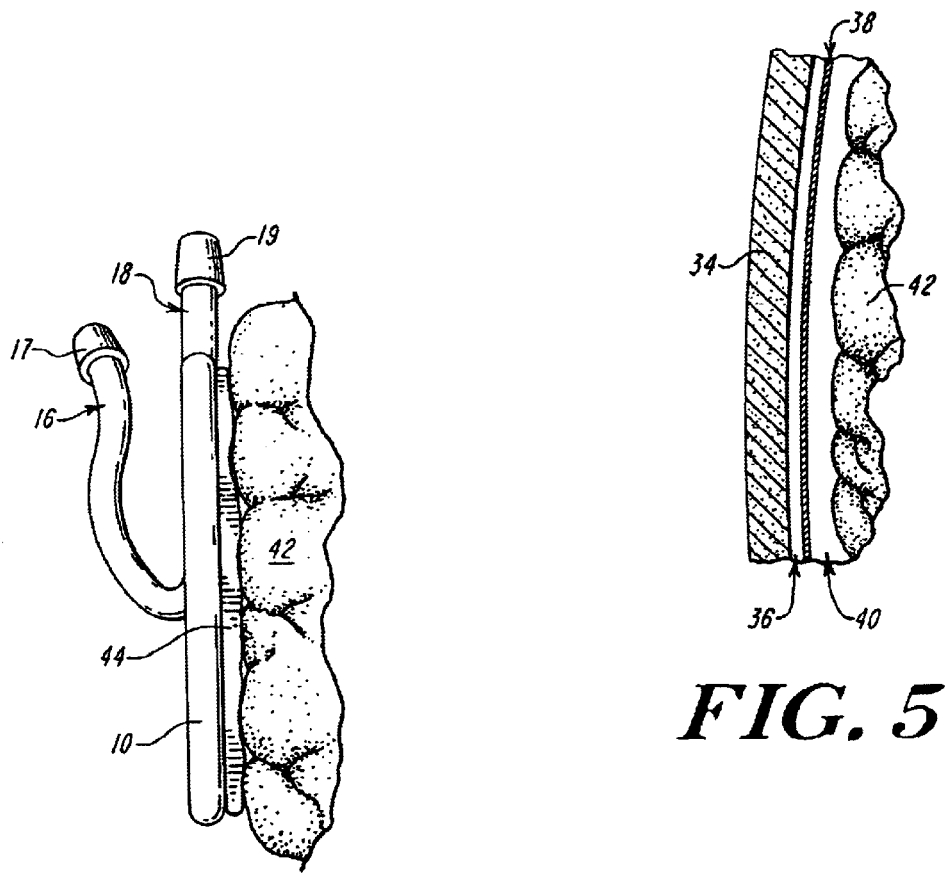
*FIG. 6*
*FIG. 5*

METHODS AND APPARATUS FOR THERMALLY AFFECTING TISSUE

CROSS-REFERENCE TO RELATED APPLICATIONS

This application claims priority from U.S. Provisional Patent Application Ser. No. 60/195,571, filed on Apr. 7, 2000, which is expressly incorporated by reference herein.

STATEMENT REGARDING FEDERALLY SPONSORED RESEARCH

Not Applicable.

BACKGROUND OF THE INVENTION

This invention pertains to methods and apparatus for thermally affecting tissue, and, more particularly, is directed to methods and apparatus for cooling brain tissue.

The medical profession has long known that the human brain is highly susceptible to injury following the reduction or cessation of blood flow thereto. Such injury often occurs, for example, following stroke, cardiac or respiratory arrest, or as a result of other bodily trauma. The medical profession also has long known that the application of cold to the human body slows the body's metabolic activity.

Based on this collective knowledge, plus the fact that brain injury usually has debilitating, irreversible consequences to a victim thereof, scientific research has focused upon inducing hypothermia to reduce the likelihood and/or extent of such brain injury.

Early research efforts (i.e., those prior to 1970) in this area focused upon global body hypothermia, in which a patient's entire body is cooled, e.g., to approximately 30–32° C., in order to concurrently cool brain tissue. In recent years, however, such techniques have been criticized by those in the art as tending to cause conditions (e.g., depression of systemic immune function, creation of cardiac arrhythmias, reduction of cardiac output) that can result in organ damage.

Consequently, more recent research in this art has focused upon achieving brain cooling through localized hypothermia. Among such research efforts are those described in U.S. Pat. Nos. 5,957,963, 5,916,242, 5,716,386, 5,531,776, and 5,474,533. Also in this vein are the approaches set forth in U.S. Pat. Nos. 3,897,790 and 3,776,241.

The U.S. Pat. No. 5,957,963 patent discloses a catheter that is placed within an artery that carries blood to the brain. Coolant is circulated into the catheter to cool the artery, thus cooling the blood flowing from the artery to the brain, and, in turn, cooling the brain itself.

The U.S. Pat. No. 5,916,242 patent discloses a collar that is worn around the neck to cool the carotid artery, thus cooling the brain via cooled blood flowing from the carotid artery to the brain. It also discloses the use of a tube that is inserted into a patient's trachea until it is in intimate contact with the back of a patient's oral cavity and, thus, in contact with blood vessels located thereat. Coolant is then flowed into the tube to cool the blood vessels, which carry cooled blood into the brain.

The U.S. Pat. Nos. 5,716,386, 5,531,776, and 5,474,533 patents are directed to devices that are positioned within the esophagus such that a heat transfer surface of the device is juxtaposed with a thoracic vessel. Coolant is then pumped through the device to cool the blood contained in the thoracic vessel, which, in turn, flows into and lowers the temperature of a patient's cerebellum.

The U.S. Pat. Nos. 3,897,790 and 3,776,241 patents disclose a technique for achieving brain cooling by locally irrigating the surface area of the nasal mucosa in order to cool the temperature of blood destined for the cavernous sinus which is in proximity to the brain.

Although such techniques are perhaps effective to manipulate brain temperature, they are likely highly inexact. This is because, for example, even after one ceases cooling one or more arteries or vessels using such techniques, the blood being carried to the brain via the vessel(s) or artery/arteries will continue to cool brain tissue for a residual time period until the blood returns to its normal temperature. Furthermore, by cooling specific vessels, one merely cools brain tissue closest to those vessels and their major arteries.

Therefore, a specific need exists for methods and apparatus that are capable of achieving safe, effective and precise localized brain cooling.

Moreover, a general need also exists for methods and apparatus that allow safe, effective and precise thermal affecting (i.e., temperature manipulation) of tissue.

SUMMARY OF THE INVENTION

The present invention provides methods and apparatus for thermally affecting (i.e., manipulating the temperature of) tissue. Although the invention is primarily shown and described in conjunction with cooling brain tissue, it is understood that the methods and apparatus of the present invention may be used to thermally affect (i.e., to raise and/or lower the temperature of) any tissue.

In one aspect of the invention, a thermally affecting device is provided as a closed device wherein thermally transmissive fluid is circulated through the device, an outer surface of which is configured to directly contact tissue to thermally affect the tissue. In another aspect of the invention, the thermally affecting device is provided as an open device wherein thermally transmissive fluid is circulated through the device and systematically deployed directly onto tissue to thermally affect the tissue. For example, the device may be placed either within, or in proximity to, epidural or subdural brain space in order to thermally affect brain tissue.

In either aspect of the invention, the device may include one or more temperature and/or pressure measuring elements to measure the temperature/pressure of the thermally transmissive fluid and/or that of the tissue being thermally affected. Moreover, both the closed and open devices may be placed at or near tissue via an existing passage into the body, or by creating an opening specifically for placement of the device. Optionally, a retraction device may be employed in order to facilitate the placement of the device at a tissue site.

BRIEF DESCRIPTION OF THE DRAWINGS

The invention will be more fully understood from the following detailed description taken in conjunction with the accompanying drawings, in which:

FIG. 4 is a front view of a human head following placement of the device of FIG. 1 on the brain;

FIG. 5 is a view of the area of a human head between the scalp and the brain;

FIG. 6 is an enlarged view of the device of FIG. 4 following placement thereof on the brain;

DETAILED DESCRIPTION OF THE DRAWINGS

The present invention provides methods and apparatus for thermally affecting (i.e., raising or lowering the temperature or other thermal characteristic of) tissue. The apparatus can be in the form of either a "closed" device (see FIGS. 1–11) or an "open" device (see FIGS. 12–15). In each of the closed device embodiments, thermally transmissive fluid is circulated into the device, an outer surface of which is adapted for direct thermal contact with tissue to thermally affect the tissue. In each of the open device embodiments, thermally transmissive fluid is circulated through the device and systematically deployed directly onto tissue to thermally affect the tissue.

FIGS. 1–11 depict exemplary closed devices in accordance with the present invention. Such closed devices include a substantially fluid-tight implantable member 10, an outer surface 12 of which is placed on or against tissue. The implantable member 10 also includes one or more internal lumens or flow passages 14 (see FIGS. 2 and 3) through which thermally transmissive fluid is circulated in order to thermally affect a tissue site.

Figure 1:
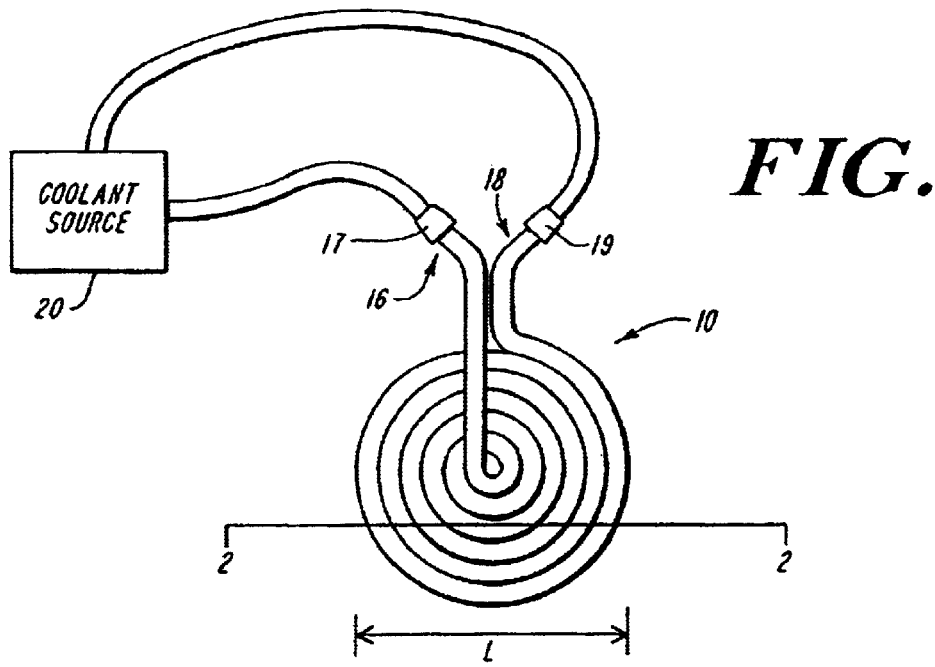
FIG. 1 is a top view of an embodiment of a closed device in accordance with the present invention.

The internal lumen or conduit 14 has an entry port 16 into which thermally transmissive fluid enters from a fluid source 20, and an exit port 18 from which thermally transmissive fluid exits and either is routed back to the fluid source or to a collection area (not shown). As shown in FIG. 1, either or both of the entry port 16 and exit port 18 may include a connector 17, 19, such as a medical quick-connect fitting, to entirely prevent, or to substantially deter, leakage of thermally transmissive fluid upon its entry into, and exit from, the internal conduit 14.

Thermally transmissive fluid is directed into the entry port 16 and out of the exit port 18 of the internal lumen 14 by suitable equipment/source generally known in the art, e.g., via a circulating pump. The temperature of the fluid source (and, therefore, the thermally transmissive fluid emerging therefrom) is controlled as is generally known in the art, e.g., by heating or refrigeration in conjunction with a set point controller. Exemplary fluids include, but are not limited to, one or more liquids, gases, or combinations thereof.

In an embodiment in which the thermally transmissive fluid is coolant and the tissue being thermally affected is brain tissue, the coolant should be a flowable material that can tolerate a temperature range of between about 50° C. and −10° C. Exemplary coolants in such embodiments include, but are not limited to, liquids and fluids such as water, electrolyte solutions (e.g., saline), or antifreeze solutions.

The implantable member 10 is shaped to maximize the area of its outer surface 12 that contacts the tissue site upon implantation. As shown in FIG. 1, the implantable member 10 may be substantially circular in shape, wherein the internal conduit 14 has been looped around itself to resemble a coil. The implantable member 10 may have other shapes while still being able to effectively thermally affect tissue. Such shapes include, but are not limited to, substantially elliptical, substantially oval, substantially square, substantially trapezoidal, or substantially rhomboid.

The exact material and/or dimensions of the implantable member 10 may vary depending on several circumstances, such as the desired thermal effect on the tissue, the specific tissue to be thermally affected, etc. The implantable member 10 is generally formed of a flexible, heat conductive, biocompatible material, such as a silicone elastomer, e.g., silastic tubing, but may be formed of other suitable materials.

Figure 2:
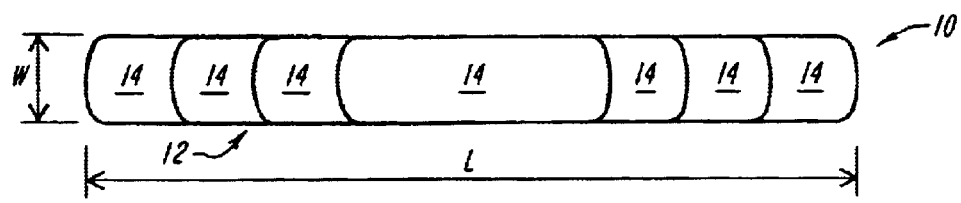
FIG. 2 is a sectional view of the device of FIG. 1 taken along line 2—2.
Figure 3:
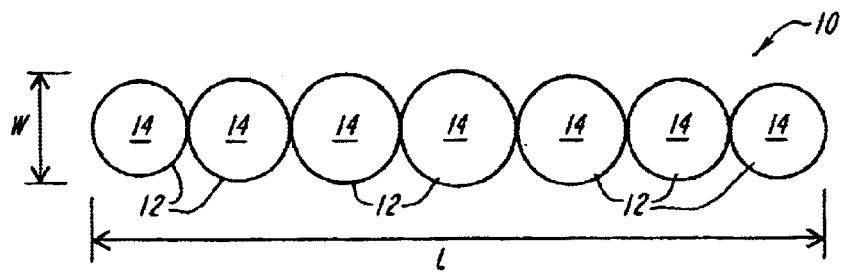
FIG. 3 is an alternate embodiment of the device of FIG. 2.
Figure 7:
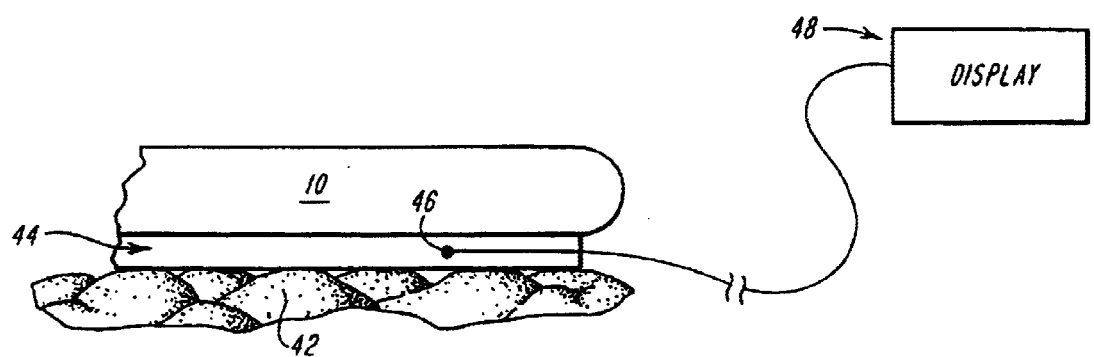
FIG. 7 is a further enlarged view of the device of FIG. 6 with a temperature measuring element attached to the backing sheet of the device.

In an embodiment in which the implantable member is used to thermally affect brain tissue, the cross-sectional length, L, of the implantable member 10 is generally between five millimeters and twenty-five centimeters. Additionally, the cross-sectional width, W, of the implantable member 10 may be substantially uniform as shown in FIG. 2, or may non-uniform, e.g., as shown in FIG. 3.

The device 10 of FIG. 1 is shown in FIGS. 4–6 having been implanted on or against brain tissue. In order to implant the device as such, the skin and scalp layers 32 and skull 34 of a patient 30 are penetrated. Once this has occurred, the epidural space 36, and, optionally, the dura matter 38 and the subdural space 40, are penetrated such that the brain 42 is revealed. Techniques for penetrating the skin and scalp layers 32, the skull 34, the dura matter 38 and the subdural space are generally known in the art.

The device 10 may either be placed epidurally, wherein it is placed between the skull and the dura 38 (i.e., in epidural brain space 36), or subdurally, wherein it is placed between the dura and the surface of the brain cortex (i.e., in subdural brain space 40). In order to better illustrate these portions of the human head 30, the brain 42 and the areas of the head which surround it are also shown in FIG. 5 prior to implantation of the device 10.

Although not shown in the drawings, it is understood that placement of the device 10 at loci other than brain tissue in order to thermally affect other tissue sites can be accomplished by placing the device within one or more existing work areas within a patient, or by surgically (or otherwise) penetrating a patient to define a passage and work area of appropriate size and shape to allow for placement of the device.

As shown in FIG. 6, a backing sheet or pad 44 can be attached (e.g., via an adhesive) to the implantable member 10 such that the backing sheet lies between the implantable member and the tissue 42 that is being thermally affected. The backing sheet 44 should be made of a material that conducts heat and that will not adhere to the tissue surface 42 (i.e., to facilitate removal of the device without damaging the tissue surface). Exemplary such materials include, but are not limited to, silicone.

The backing sheet 44 will generally have a temperature measuring element 46 (see FIG. 7) attached thereto. This element 46 provides a temperature measurement at the backing sheet 44 area, thus providing a reliable estimate of the surface temperature of the tissue 42 being thermally affected by the device.

The temperature measurement element 46 may be connected to a suitable temperature indication element 48, such as a display, as is generally known in the art (e.g., via an analog-to-digital converter) in order to provide a temperature indication. In other embodiments, the device 10 need not include a backing sheet 44, and, in such embodiments, the temperature measuring element 46 (if included) can be attached to the device itself.

Figure 8:
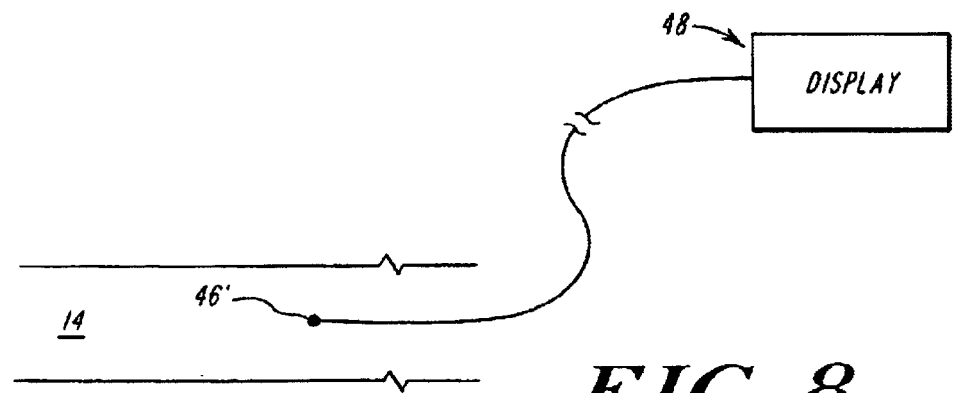
FIG. 8 is an enlarged view of the device of FIG. 1 or 6 with a temperature measuring element inserted within the internal conduit of the device.

As shown in FIG. 8, in addition to and/or in lieu of the temperature measurement element 46, the implantable member 10 can include one or more additional temperature measurement elements 46'. These elements 46' may be placed systematically within the internal conduit 14 of the implantable member 10 to provide temperature measurements of the thermally transmissive fluid therein.

Exemplary placement options for such temperature measurement elements 46' include at or near the entry port 16 of the inner conduit 14, and/or at or near the exit port 18 of the inner conduit, and/or at any location therebetween. The temperature measurement element(s) are connected to suitable temperature indication element(s) also as is generally known in the art.

The device of FIGS. 1–8 may be used to thermally affect tissue under many circumstances; however, use of such a device is preferred to cool brain tissue in instances following a hemicraniectomy procedure, i.e., where a portion of the skull has been removed.

A hemicraniectomy is often performed following a stroke (when, as explained above, cooling of the brain can prevent potentially devastating brain injury) in order to relieve pressure and to allow for the brain to comfortably swell—since brain swelling is a common side effect following a stroke. Thus, following a hemicraniectomy, when a portion of the skull has already been removed, the device of FIGS. 1–8 may be systematically placed at a location to provide cooling to the brain without necessitating a separate, invasive procedure.

Figure 9:
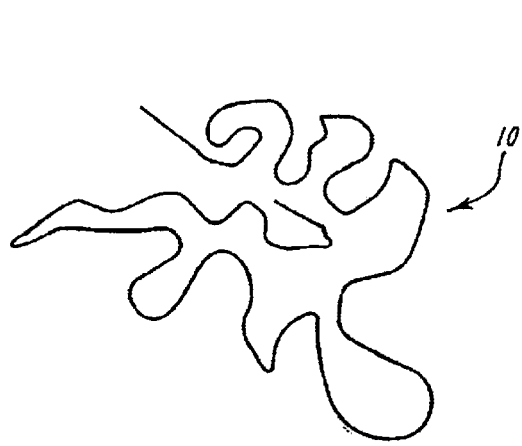
FIG. 9 is a top view of an alternate embodiment of a closed device in accordance with the present invention.
Figure 10:
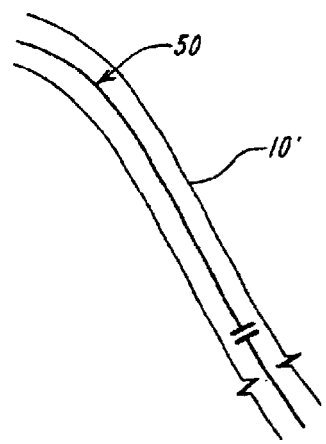
FIG. 10 is a perspective view of the device of FIG. 9 following placement thereof over a guidewire.
Figure 11:
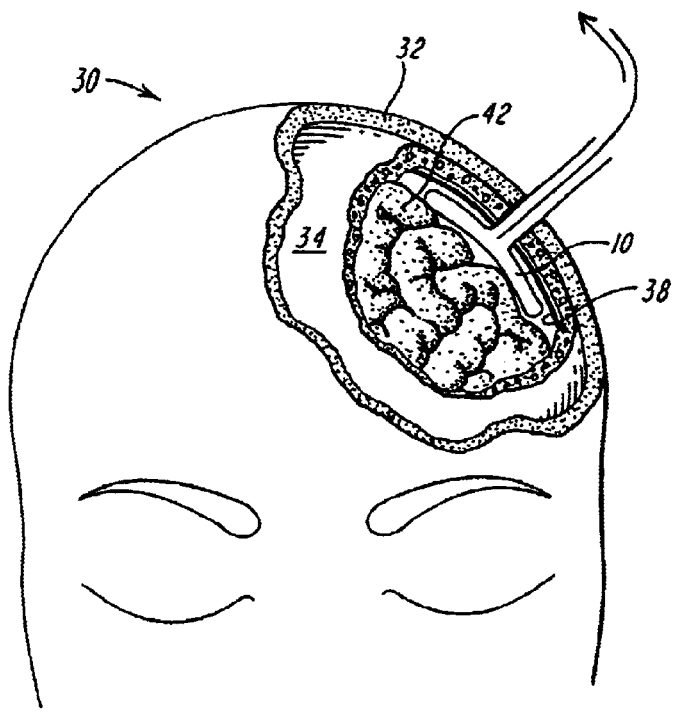
FIG. 11 is a front view of a human head following placement of the device of FIG. 10 on the brain and during retraction of the guidewire from the device.

Referring now to FIGS. 9–11, an alternate embodiment of a closed device is shown. In this embodiment, the implantable member 10' is constructed of a shape memory material, e.g., a nickel titanium alloy. Like the implantable member 10 of FIGS. 1–8, this member 10' should have an at-rest shape that allows for coverage of a large surface area of tissue. To this end, the member 10' may be a tube that is formed of shape memory material or that includes a shape memory support, e.g., a shape memory wire embedded in a silicone rubber tube. In either case, the shape memory material causes the cooling tube to spread out along a surface region of the tissue.

Prior to implantation, the implantable member 10' is placed over a guidewire, causing the member to substantially conform to the shape of the guidewire (see FIG. 10), thus facilitating the positioning of the member within the skull (or other work area). As shown in FIG. 11, the guidewire is fed into a passageway in the skull (or other defined opening leading into a work area) and placed at a desired location on the brain (or other tissue site) either epidurally or subdurally as described above. The guide wire is then removed (as shown by the arrow in FIG. 11), allowing the implantable member to return to its at-rest shape (as depicted in FIG. 9) at the desired location on or against the brain or other tissue site.

The shape memory device 10' depicted in FIGS. 9–11 may be used under any circumstances, but its use is preferred for minimally invasive circumstances because it requires the existence or preparation of a smaller passageway to the tissue site (i.e., work area) than, for example, the device depicted in FIGS. 1–8.

Figure 12:
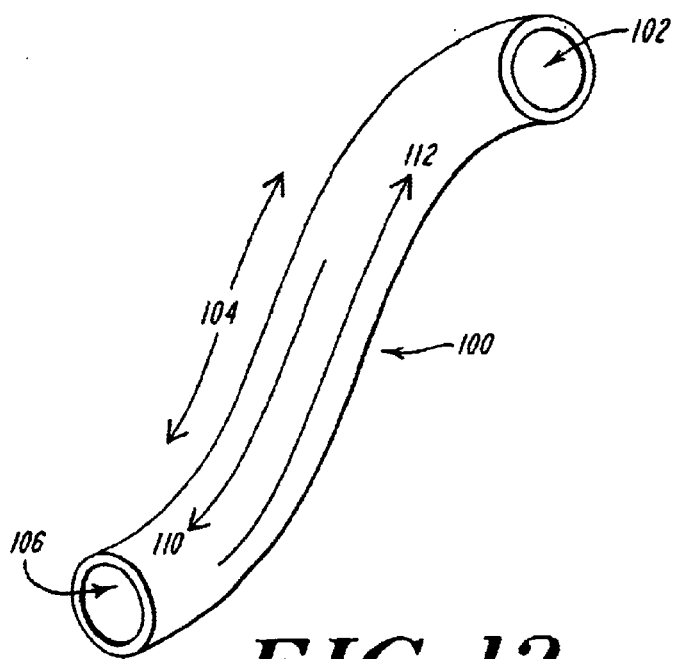
FIG. 12 is a perspective view of an open device in accordance with the present invention.
Figure 13:
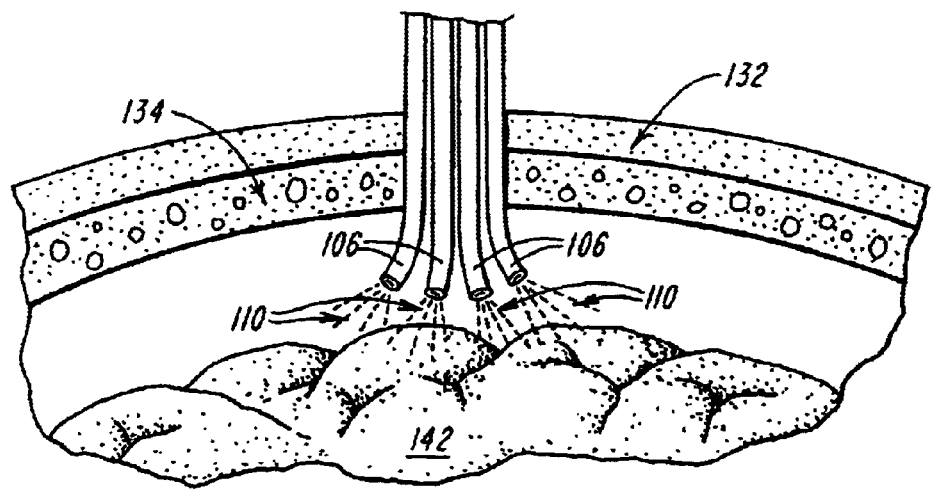
FIG. 13 is a view of a plurality of the FIG. 12 devices following placement proximate to a brain and during deployment of coolant from the devices.
Figure 14:
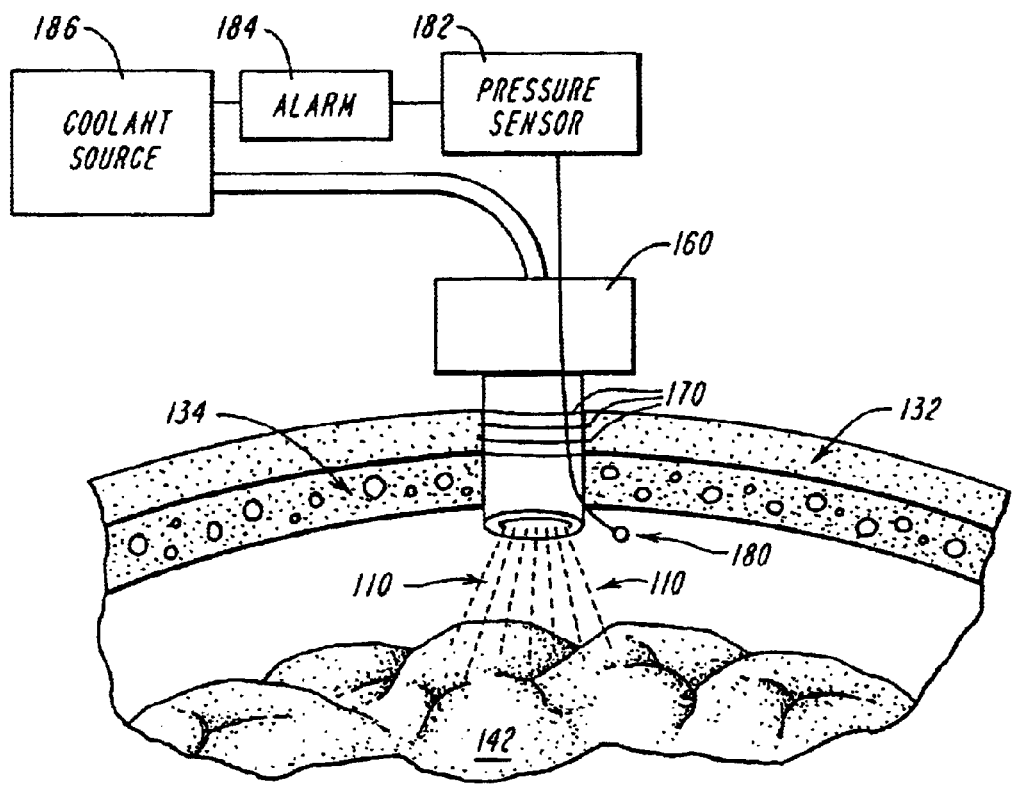
FIG. 14 is a front view of a human head during insertion of a manifold containing a plurality of the FIG. 12 devices.

Referring now to FIGS. 12–14, an embodiment of an open device for thermally affecting tissue is shown. The device includes a plurality of catheters (such as the exemplary catheter of FIG. 12), each of which is inserted proximate tissue. Once inserted, all or some of the catheters deploy thermally transmissive fluid directly onto the tissue. The thermally transmissive fluid is subsequently retrieved via one or more separate suction tubes and/or via a suction force exerted through one or more of the catheters. Alternatively, a separate opening or manifold may be positioned to define suction openings proximate the thermally transmissive fluid supply openings, thus providing a thermally transmissive fluid flow region over a desired surface region of the tissue.

The exemplary catheter 100 of FIG. 12 includes an entry port 102 into which thermally transmissive fluid is supplied in the manner generally as described above with respect to the device of FIGS. 1–8. Thermally transmissive fluid 110 flows through an internal conduit 104 of the catheter 100 and out an exit port 106 to thermally affect tissue as shown in FIG. 13. Thereafter, a suction force 112 may be exerted through the internal conduit 104 of the catheter to retrieve dispersed thermally transmissive fluid via the exit port 106.

Although the catheter of FIG. 12 is depicted with one conduit 104 through which thermally transmissive fluid 110 is deployed and through which a suction force 112 is exerted, e.g., a single lumen catheter, it is understood that the catheter may instead have separate internal conduits for the simultaneous or non-simultaneous deployment of thermally transmissive fluid, and for the exertion of suction force.

FIG. 13 depicts a plurality of catheters 100 having been placed within the scalp 132 and skull 134 of a patient and in proximity to the patient's brain tissue 142 as is generally known in the art. The number of catheters 100 may vary based on a number of factors, including, but not limited to, the desired temperature and the area of brain tissue to be cooled. Generally, each catheter has a substantially constant diameter that is between about 0.1 millimeter and 10.0 millimeters, and a length that is greater than its diameter.

One, some or all of the catheters deploy thermally transmissive fluid 110 from their exit ports 106 to thermally affect tissue 142. While or after this occurs, one, some or all of the catheters may be operated as vents or suction returns to retrieve thermally transmissive fluid 110 from the tissue area 142. Exemplary thermally transmissive fluids include water, saline or a mixed fluorocarbon solution. The mixed fluorocarbon solution may be compounded such that it is deployed in liquid form, wherein the liquid undergoes a phase change and transforms to a gas at a tailored boiling point.

The fluorocarbon solution is capable of extracting heat at a high rate per unit volume during its transition from liquid to gas, thus effectively "cooling" the tissue site. This phase transition may be controlled as is generally known in the art to prevent an excessive, and, therefore, potentially harmful, temperature drop. Use of a fluorocarbon solution is further advantageous due to the ease spreading and extraction of a gas, as compared to a liquid, and due to its low viscosity.

Additionally, the thermally transmissive fluid 110 can include a pharmaceutical, neuroprotective agent, e.g., an enzyme inhibitor or a neuro-chemical receptor antagonist/agonist, to ensure that the thermally transmissive fluid does not harm the tissue or surrounding areas which the thermally transmissive fluid may contact.

The plurality of catheters 100 may be used in any circumstance in which a passageway to the tissue site already exists (e.g., following a hemicraniectomy) or can be fashioned.

In an exemplary embodiment depicted in FIG. 14, the plurality of catheters 100 may be attached to a manifold 160, which itself is attached to an opening made in the skull as is generally known in the art. By way of non-limiting example, the manifold 160 may have a plurality of threads 170 to allow it to be threaded into the skull, and may be configured so that the catheters 100 can be advanced through the manifold and proximate the brain 142 to release coolant therefrom.

The exemplary embodiment of FIG. 14 (and or any other embodiment of the invention) may also include features that protect against damage caused by excess pressure levels at the tissue treatment site. For example, the device may include a pressure measuring element 180, e.g., a pressure transducer, in communication with a pressure indication element 182 such that the pressure at the tissue treatment site is known.

The pressure indication element 182, in turn, may be in communication with an alarm or other visual, audio, or audio/visual warning indicator 184 that is effective to signal an operator to cease or reduce the flow of thermally transmissive fluid from the fluid source 186. Such a warning system to warn of unacceptably high or low pressure levels at the brain tissue treatment site.

Figure 15:
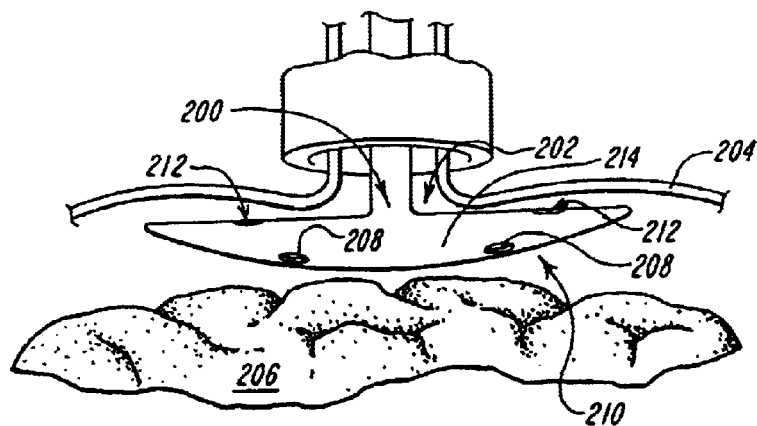
FIG. 15 is a view of an alternate embodiment of an open device in accordance with the present invention.

Other "open" implementations effective to thermally affect a tissue site/region are also possible. For example, as shown in FIG. 15, a mushroom- or umbrella-shaped catheter 200 may be delivered/inserted through a small opening 202 and positioned within a patient's body (e.g., via a guidewire insertion system as described above with respect to FIGS. 9–11), until it is in proximity to a tissue site 206 (e.g., brain tissue). Such a catheter 200 includes at least one opening 208 on its tissue surface 210 to irrigate the tissue 206 with thermally transmissive fluid. It further includes at least one opening 212 on a tissue opposing surface 214 to provide a suction return for dispersed thermally transmissive fluid.

In embodiments in which the device 200 is used to cool brain tissue, this location of the suction openings 212 is preferred because it prevents suction of delicate brain tissue 206. Further, any of the thermally transmissive fluid distribution devices described above may include a protective jacket or cage that also is effective to prevent clogging of suction return openings with tissue (e.g., brain tissue and/or dura matter).

The placement of any of the devices described above may be facilitated through the use of a retraction device. For example, such a retraction device may be utilized to separate brain tissue that is to be treated from its protective dura matter (i.e., to clear space within the subdural space).

Figure 16A:
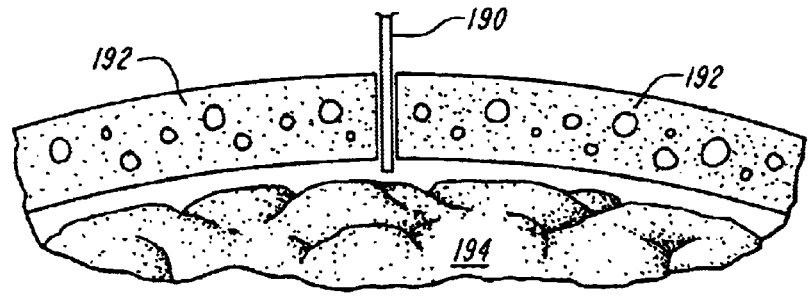
FIG. 16A is a front view of a retraction device following its insertion into the skull but prior to its having retracted brain tissue therefrom.
Figure 16B:
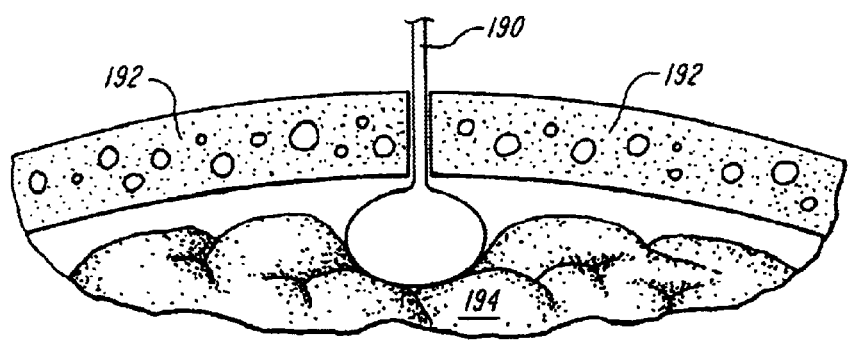
FIG. 16B is a front view of the retraction device of FIG. 16A following it having retracted brain tissue from the skull.

FIGS. 16A and 16B depict an exemplary retraction device 190, which is placed within the skull 192 in a deflated or non-expanded/non-deployed condition (see FIG. 16A).

Once the device 190 reaches a brain tissue site 194, the retraction device 190 is inflated or otherwise caused to expand (see FIG. 16B), wherein it creates space between the skull 192 and the brain tissue site 194 to provide a clearance for the insertion of the thermally affecting device.

It is understood that the retraction device 190 may be incorporated into a temperature affecting catheter, e.g., the device of FIGS. 12–14, such that the device 190 is placed within a lumen of the catheter. The device 190 is inflated, expanded, or deployed to provide a clearance area, then deflated or otherwise caused to return to its non-expanded state, and then removed to leave room for the thermally transmissive fluid to flow.

Another type of retraction device (not shown) includes a port out of which saline (optionally mixed with a pharmaceutical neuroprotective agent as described above) may be infused at a rate and volume sufficient to gently push away the tissue to be treated (e.g., to push away brain tissue from the dura) to create space for the insertion of the thermally affecting device. One of ordinary skill in the art will appreciate that still further retraction devices may also be used in conjunction with any or all of the thermally affecting devices described herein.

In any of the above-described embodiments of the invention, the implantable member 10, 10' may have a single lumen or multiple lumen arrangement. In a multiple lumen arrangement having two lumens, thermally transmissive fluid is able to flow from a fluid source through a first lumen, while also being capable of simultaneously flowing via suction or other means back through the member via a second lumen in order to return to the fluid source. Other multiple lumen arrangements may alternately be used, including, but not limited to, concentric lumens, a single lumen divided into hemispherical chambers, or side-by-side lumen arrangements.

EXAMPLES

The device of FIGS. 1–8 has been tested on the brain tissue of five dogs. Dogs were chosen because their brains are most readily scalable to human brains on a per unit volume basis. Also, the literature provides known stroke models for dogs.

Five dogs underwent unilateral craniotomy under general anesthesia to expose their cerebral cortexes. Cooling devices of the type depicted in FIGS. 1–8 were then applied to the brain, which has a normal (i.e., not stroked) temperature of approximately 39.3° C.

Following baseline measurements, the surface of the brain tissue to which the device had thermal contact were found to have been cooled to approximately 26.5° C., reflecting a 13° C. difference relative to contralateral hemisphere controls. Furthermore, thermocouples attached to the devices revealed that brain tissue approximately 10 millimeters below the surface of the brain tissue had been cooled approximately 3° C. from its pre-cooling temperature.

These results demonstrate the ability of such devices to induce effective cooling in healthy brain tissue, and, therefore, in brain tissue following stroke, wherein blood flow into the brain has been curtailed or eliminated, thus making the brain less resistant to cooling.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An apparatus for thermally affecting brain tissue, comprising:

an implantable member having an outer surface configurable to contact target brain tissue;

at least one fluid-tight lumen defined by the implantable member, the fluid-tight lumen being in thermal communication with the outer surface of the implantable member and being configured to receive a thermally transmissive cooling fluid to thereby impart a thermal change to the outer surface of the implantable member;

a first temperature sensing element that is effective to measure the temperature of the target tissue; and a pressure measurement element having a first end positioned in proximity to the implantable member and effective to measure the pressure at which the implantable member is applied to the target tissue, whereby the implantable member is adapted for thermally transmissive contact with epidural brain tissue.

2. The apparatus of claim 1, wherein the thermally transmissive cooling fluid is selected from the group consisting of liquid, gas and a combination thereof.

3. The apparatus of claim 1, wherein the implantable member has a shape selected from the group consisting of substantially circular, substantially elliptical, substantially oval, substantially square, substantially trapezoidal and substantially rhomboid.

4. The apparatus of claim 3, wherein at least a portion of the implantable member is looped around itself to approximately resemble a coil shape.

5. The apparatus of claim 1, wherein the implantable member is formed from a flexible, thermally conductive, biocompatible material.

6. The apparatus of claim 5, wherein the implantable member is formed from a silicone elastomer.

7. The apparatus of claim 1, wherein the implantable member is adapted for direct thermally transmissive contact with subdural brain tissue.

8. The apparatus of claim 1, further comprising:

a backing member attached to the implantable member such that the backing member is in thermal contact with the tissue.

9. The apparatus of claim 8, wherein the backing member is made of a thermally transmissive material, the thermally transmissive material being resistant to adherence to the tissue.

10. The apparatus of claim 9, wherein the backing member is made of silicone.

11. The apparatus of claim 1, further comprising:

a second temperature measurement element positioned within the lumen and effective to measure the temperature of any fluid within the lumen.

12. The apparatus of claim 1, wherein the pressure indication element is in communication with a warning indicator such that the warning indicator is effective to produce a signal upon the measurement of a predetermined pressure level by the pressure measurement element.

13. The apparatus of claim 12, wherein the signal is selected from the group consisting of a visual signal, an audio signal, and a combination thereof.

14. The apparatus of claim 1, wherein the implantable member is constructed of a shape memory material.

15. The apparatus of claim 1, wherein the first temperature sensing element is positioned on a tissue-contacting portion of the implantable member.

16. The apparatus of claim 8, wherein the first temperature sensing element is positioned on the backing member.

* * * * *